United States Patent [19]

Gaskin

[11] Patent Number: 5,256,403
[45] Date of Patent: * Oct. 26, 1993

[54] COMPOSITION AND METHOD FOR PROTECTING THE SKIN FROM UV-RAYS

[76] Inventor: Frances C. Gaskin, 298 State St., Albany, N.Y. 12210

[ * ] Notice: The portion of the term of this patent subsequent to Feb. 21, 2006 has been disclaimed.

[21] Appl. No.: 638,695

[22] Filed: Jan. 8, 1991

Related U.S. Application Data

[60] Division of Ser. No. 263,039, Oct. 26, 1988, Pat. No. 5,006,331, which is a continuation-in-part of Ser. No. 600,635, Jan. 5, 1987, Pat. No. 4,806,344.

[51] Int. Cl.$^5$ .......................... A61K 7/06; A61K 7/42; A61K 7/44; A61K 7/48
[52] U.S. Cl. ......................................... 424/59; 424/60; 424/70; 514/865; 514/886; 514/887; 514/928; 514/969; 514/880; 514/881
[58] Field of Search ............................................ 424/59

[56] References Cited

U.S. PATENT DOCUMENTS 4,806,344  2/1989  Gaskin .................................. 424/59

Primary Examiner—Dale R. Ore
Attorney, Agent, or Firm—Hamilton, Brook, Smith & Reynolds

[57] ABSTRACT

Solubilized melanin based compositions supply melanin to skin, scalp and/or hair. The compositions consist of melanin, as an active ingredient, and a substance to solubilize the melanin blended together in a vehicle suitable for topical application. A melanin-based composition applied to the skin provides photoprotection of the human epidermis from exposure to ultraviolet rays. A melanin-based composition applied to wounds in the skin accelerates healing of the wounds. A melanin-based composition applied to the hair and scalp strengthens the hair.

11 Claims, No Drawings

COMPOSITION AND METHOD FOR PROTECTING THE SKIN FROM UV-RAYS

RELATED APPLICATIONS

This application is a division of 07/263,039, filed on Oct. 26, 1988, now U.S. Pat. No. 5,006,331 which continuation-in-part of U.S. Patent Application, Ser. No. 000,635, filed on Jan. 5, 1987, for a "Sun Protectant Composition and Method", now U.S. Pat. No. 4,806,344.

BACKGROUND OF THE INVENTION

The sensitivity of the human skin to the ultraviolet rays (UVR) of the sun is determined by the amount of the pigment melanin contained within the skin. Many individuals with fair or light/white complexions (Skin Types I, II, III) burn because they do not produce sufficient melanin to protect the skin against sunburn. Moderately brown to dark skinned persons (Skin Types IV, V, VI) are not entirely protected from the deleterious effects of solar radiation. Skin Type I-always burns easily (freckles) and never tans; Skin Type II-always burns easily and tans minimally; Skin Type III-burns moderately and tans gradually; Skin Type IV-burns minimally and tans well; Skin Types V and VI-tan profusely but rarely burn.

In addition to sunburn, long-term exposure to the sun, particularly for individuals who do not produce sufficient melanin such as Skin Types I, II, III can lead to premature aging of the skin and cutaneous cancer, usually basal cell, squamous cell carcinomas and malignant melanomas. Dark skinned persons do develop skin cancer but in small percentages, for example, malignant melanomas may occur in areas of the body where melanin levels are low, such as the palmar surfaces of the hands and the plantar surface of the feet. Conditions such as allergic reactions, coarseness, dryness, mottling, flaccidity and blemishes are also effects of long-term exposure. To obviate these detrimental effects, experts in the field have suggested sun protection formulas having various combinations and percentages of chemical, physical and natural sunscreens, with the sun protective factor (SPF) ranging from 2 to 30, that is, minimal sun protection to ultra sun protection. Further, melanin precursors-tyrosine, tyrosinase and 3,4-Dihydroxy Phenylalanine (DOPA) are included in suntan preparations to stimulate the production of melanin. Yet, each year these harmful or life-threatening toxicities are increasingly becoming more Widespread because the problem still exists for those persons who do not genetically possess sufficient melanocytes (pigment cells).

The pigment cell colors the skin by injecting melanosomes into keratinocytes. The keratinocyte carries its burden of pigment to the stratum corneum where it is shed as melanin dust. Melanin provides effective protection against actinic damage of the sun. Notably, there exists an increased correlation between skin sensitivity to UVR and melanin content. The degree of sunburn reaction, prevalence of abnormal photosensitivity and the degenerative (aging) and neoplastic changes are reduced with increasing melanin pigmentation. This increased relationship is correlated to the distribution of melanosomes and quantity of melanin in the epidermis. The SPF estimates of melanin have been cited as 1.0-4.3 to 5 for Skin Types I through Skin types V and VI, respectively.

The photoprotective role of melanin is related to its physical and biochemical properties; melanin (a) scatters and degrades radiation to heat, (b) absorbs the radiation and promotes immediate oxidation reaction, and (c) quenches free radicals generated by UVR. Further, melanin in the human epidermis functions as a stable free radical. Because of its polyquinoid nature, melanin acts as an electron exchange polymer and therefore is capable of undergoing an immediate photo-oxidation or darkening reaction. Melanin quenches the formulation of other types of damaging free radicals in the human epidermis upon exposure to UVR. This property of melanin to serve as a scavenger for damaging non-melanin free radicals may significantly contribute to its photoprotective role in individuals of Skin Types IV, V and VI.

The exposure to UVR itself, produces a phototherapeutic advantage. Subsequent to three exposures, the Type IV, V, VI skin become less likely to sunburn, However, Type I, II, III individuals develop very few melanized melanosomes. A melanin filter never develops in the stratum corneum resulting in an absence of melanin dust in the epidermis. Therefore, the need exists for the formulation of the topical application of melanin to provide an added amount of melanin in the skin to protect the human skin from the UV rays of the sun. Yet, dissolving melanin in solution or otherwise distributing melanin in a mixture suitable for topical application for delivery of melanin into the skin has been a difficult problem in the past.

SUMMARY OF THE INVENTION

The present invention relates to a sun protectant composition and method of dissolving melanin in a composition for the purpose of supplying melanin to the skin to provide photoprotection of the human epidermis from exposure to ultraviolet rays. The ingredients of the composition are non-mutagenic and non-allergic and can be topically applied to the human skin including the scalp. More specifically, the composition of the present invention comprises an effective amount of solubilized melanin blended in a cosmetic base having a sunscreen and an ingredient such as beta-carotene for absorbing free radicals generated upon exposure of the skin to ultraviolet rays. Preferably, the melanin is solubilized by triethanolamine and oxidized by ferric chloride. This mixture, as well as other ingredients, are combined to make a sun protectant lotion, cream or ointment that protects the skin against ultraviolet rays or rays of the sun.

This invention also relates to a method of protecting human skin against ultraviolet rays wherein the above described sun protectant composition is topically applied to the skin and thereupon provides the penetration of melanin into the skin.

Equally advantageous results are obtained from the application of compositions of solubilized melanin to hair and to wounds in the skin including burns. In the former, solubilized melanin prevents oxidation of hair follicles and provides a lubricant to the hair which prevents moisture from penetrating into the hair. By accomplishing the foregoing, the melanin composition strengthens the hair sufficiently to prevent breakage under everyday tension such as during combing. In the latter, solubilized melanin acts as an oxidant and provides concentration of oxygen to the wound to inhibit the growth of microorganisms and thus accelerate healing.

In a preferred embodiment, the wound healing composition comprises an effective amount of melanin solubilized by triethanolamine, oxidized by ferric chloride and carried in a base having aloe vera and light mineral oil or similar ingredients suitable for application to the skin.

The hair strengthening composition comprises an effective amount of solubilized melanin, carried in a silicone or similar base suitable for application to the hair, such as a general shampoo, conditioner, cream rinse or pomade.

DETAILED DESCRIPTION OF THE INVENTION

A melanin composition of the present invention for protecting the skin from the ultraviolet rays of the sun or other sources of ultraviolet rays comprises melanin as the active ingredient. The melanin is solubilized by a suitable ingredient such as triethanolamine and oxidized by a suitable chemical such as ferric chloride. The solubilized and oxidized melanin (i.e. the resulting suspension mixture of melanin, triethanolamine and ferric chloride) is subsequently mixed with ingredients to make a preparation of lotion, cream or ointment or other forms (e.g. powder) suitable for topical application to the human skin.

In an alternative method, the melanin may be rendered water soluble by mildly hydrolyzing the melanin using Trypsin in an alkaline medium. Although the hydrolysis takes place under strongly alkaline conditions, the solubilized melanin may be adjusted to nearly any cosmetically acceptable pH afterward and no unwanted materials, such as the triethanolamine are present.

Ingredients which form a vehicle suitable for topical application to the skin, such as a cosmetic base, and in Which the melanin mixture can be suspended include ingredients selected from a group consisting of 1, 2, 3 trihydroxypropane, 4-paraminobenzoic acid, 2-hydroxy-4-methoxyl-phenyl, 2-amino 3-p-hydroxyphenyl-propanoic acid, hydroxyethane, 1-hexadecanol, 7-dehydrocholesterol, carbopol gel, miglyol-gel-B, octyldimethyl PABA, d-Panthenol, glyceryl, dimethylpolysiloxane, petrolatum, mineral oil, jojoba oil, mink oil, aloe vera, preservatives, vitamins and minerals such as riboflavin and fragrance. These ingredients can be used in varying concentrations ranging from about 0.5 ml to 20.0 ml and about 0.5 mgm to 2.0 mgm and can be used in various combinations to make a composition of a desirable form (i.e. lotion, cream or ointment) of the present invention. For example, the ingredients can be varied to provide a composition whose SPF ranges from about 1 to about 30. In the examples disclosed hereafter, particular combinations of ingredients are used to prepare a sun protective factor (SPF) up to about 15.

Individually, the vehicle for topical application or cosmetic base ingredients may serve to penetrate the cellular structure of the epidermis, lubricate, screen or block as Well as protect the skin from the harmful rays of the sun.

In the final preparation, melanin is present at a concentration of from about 0.001% to about 0.09% by weight. Triethanolamine is present at a concentration of about 5% and greater, by weight and ferric chloride from about 0.0001% to about 0.27% by weight. The ingredients forming the melanin mixture may be blended with ultrasound or by other agitation means for about 2-3 hours to break up, disperse and solubilize the conglomerates.

Further substances can be added such as beta-carotene and petrolatum to protect the skin from harmful ultraviolet rays where the former absorbs free radicals generated upon exposure of the skin to ultraviolet rays and the latter blocks ultraviolet rays from the sun. Other sun screening agents may similarly be included in the composition. Such sun screening agents may be selected, for example, from the sun screening agents considered safe and effective by the Federal Drug Administration as of 1978 listed along with dose limit percentages in the U.S. application to which this application is a continuation-in-part and herein incorporated by reference.

The value of the final preparation can be enhanced by repeated applications of said composition to the skin before and during exposure to indoor solar simulators and outdoor sunlight. is understood that the cosmetic base in lotion, cream or ointment form can be differently prepared according to known methods and formulas in the art to provide a suitable carrier for the melanin mixture. The following provide specific examples and are meant for purposes of illustration and not limitation.

EXAMPLE 1. Sun Protectant Ointment, SPF about 15

1.0% by weight aloe vera, 5.0% by weight Octyldimethyl PABA, 4.5% by weight ceteary1 octanoate, 0.5% d-Panthenol were mixed slowly into 80% by weight Miglyol-Gel "B" (Caprylic/capric triglyceride stearalkonium hectorite and propylene carbonate, from Huls America, Inc., Rockleigh, N.J.). The resulting mixture was then heated to 40° C. and cooled while stirring. 0.3% fragrance was added. 0.03% beta-carotene and 8.67% mineral oil were ground together, and the previous resulting mixture was added to the ground oil mixture a little at a time.

A melanin suspension was prepared by mixing 1.5 mg melanin, 2.0 mg ferric chloride and about 5.62 g triethanolamine together for two to three hours by ultrasound. The resulting suspension was added to the above mixture to produce about 100 grams of the skin protectant ointment having an SPF of about 15.

EXAMPLE 2. Sun Protectant Cream, SPF about 10

35.0% by weight Softisan 601(glyceryl cocoate, hydrogenated coconut oil and ceteareth-25, Huls America, Inc., Rockleigh, N.J.), 5.0% glyceryl, 2.0% Miglyol 812 (caprylic/capric triglyceride, Huls America, Inc., Rockleigh, N.J.) and 4.0% Octyldimethyl PABA were mixed together and heated up to 75°-80°C. Water and a preservative heated to the 75°-80° C. were then emulsified into the above mixture.

The mixture was cooled to about 30° C. and 0.3% fragrance was added. 0.02% beta-carotene was ground into 5.0% Miglyol 812 until dissolved. The resulting emulsion was then added to the cooled mixture.

A melanin suspension was prepared by mixing 1.0 mg melanin, 1.5 mg ferric chloride and about 5.62 g triethanolamine together for two to three hours by ultrasound. The resulting suspension was added to the above mixture to produce about 100 grams of the skin protectant lotion having an SPF of about 4.

EXAMPLE 3. Sun Protectant Lotion, SPF about 4

Mixture A was prepared by mixing together 4.0% by weight Glyceryl Stearate SF, 5.0% by weight Trilaureth-4 phosphates, 2.0% cetyl alcohol and 2.5% octyldimethyl PABA and heating the mixture to 75°–80° C.

Mixture B was prepared by mixing together 3.0% d-Panthenol, a preservative, 5.0% sorbitol, 15.0% Carbopol-Gel, 1% (B. F. Goodrich) and water up to about 100% by weight, and heating to 75°–80° C. Mixtures A and B were then emulsified together. The resulting mixture was cooled to about 30° C., thereupon 0.3% fragrance was added. 0.0% beta-carotene was ground into 7% Miglyol 840 (propylene glycol Dicaprylate/-Dicaprate, Huls America, Inc., Rockleigh, N.J.) until dissolved and added to the cooled mixture.

A melanin suspension was prepared by mixing 0.1 mg melanin, 0.1 mg ferric chloride and about 5.62 g triethanolamine together for two to three hours by ultrasound. The resulting suspension was added to the above mixture to produce about 100 grams of the skin protectant lotion having an SPF of about 4.

Pharmaceutical Composition

As mentioned above, a composition comprising solubilized melanin as an active ingredient may be formed and used for healing of wounds in the skin, such as pressure sores, bed sores, burns and the like. The solubilized melanin acts as a oxidant such that when the composition containing melanin is applied to the wound, an amount of melanin is absorbed by the tissue surrounding the wound before being attracted to other non-wounded areas of the skin. Thereafter, the absorbed melanin provides and directs oxygen to the tissue of the wound. By supplying oxygen to the tissue, the melanin inhibits the growth of microorganisms and aids the natural curing of torn tissue and hence the wound. Thus, application of the solubilized melanin composition provides for the acceleration in healing of the wounded tissue.

An example of such a composition containing solubilized melanin for accelerating healing is as follows. Solubilized melanin, aloe vera and preservatives are mixed together in a base suitable for topical application comprising light mineral oil and the like. The resulting mixture is applied on top of an antibiotic which has been applied to the wound.

Variations in the ingredients may be made as are common in the art. In addition, solubilized melanin may be obtained by mixing melanin, ferric chloride and triethanolamine for 2 –3 hours by ultrasound as described in the sun protectant composition. Alternatively, solubilized melanin may be obtained by an enzymatic hydrolysis of melanin described later in the hair strengthening composition.

Hair Strengthening Composition

Unlike the melanin based sun protectant composition, solubilized melanin carried in a base appropriate for application to the hair provides advantages to the hair. By way of background, upon absorption of moisture and oxidation of hair follicles, the hair experiences what is known as a reversion process in which the hair tightens and as a result curls or kinks. Such tightening of the hair causes hair to be less flexible and hence potentially easier to break under pressure. The cause of reversion after straightening is many faceted and includes the inability of a hair product or process to completely break all bonds in the hair without depilation. Typically, even the few remaining cystine bonds have strength, and the hydrogen and salt bonds become relatively powerful in light of the reduced strength of re-oxidized cystine.

In the present invention, a melanin based composition is applied to the hair to provide an amount of melanin into the scalp and to ultimately strengthen the hair. This is accomplished by the provided melanin preventing oxidation of hair follicles and in turn reducing reversion of the hair. In addition, other ingredients of the composition along with the melanin serve as a lubricant to the hair which prevents brittleness of the hair and maintains strength of the hair by preventing moisture from being absorbed by the hair.

The melanin composition further strengthens the hair by thickening the hair. Silicone or other known ingredients are included in the composition to cause the hair to swell. Such swelling thickens the hair such that the hair is not easily tightened or broken. Hence, the hair is strengthened.

Other advantages of the melanin based composition include prevention of discoloration of the hair when exposed to the sun. In hair strengthening compositions of prior art, active ingredients caused discoloration of the hair when exposed to the sun. In the present invention the amount of melanin supplied by application of the composition maintain the color of the hair under exposure to ultraviolet rays. Thus the melanin based hair strengthening composition while strengthening the hair maintains the natural color of the hair.

Generally, solubilized melanin in an amount of about 0.0015 percent by weight of the total composition is added to a typical pomade, shampoo, conditioner and/or cream rinse. A silicone based pomade, shampoo, conditioner and/or cream rinse is preferred. Particular examples of hair strengthening compositions containing solubilized melanin as the active ingredient follow.

| Ingredients | % |
|---|---|
| Shampoo | |
| Demineralized Water | 53.1485 |
| Melanin hydrolysate | 0.0015 |
| Celquat L-200 | 0.50 |
| Natrosol 250 HHR | 0.25 |
| Quat-Coll IP-10 | 3.00 |
| dl-Panthenol | 0.25 |
| Biomin Cinque | .10 |
| Germaben II-E | 1.00 |
| Aloe Extract HS | 0.10 |
| Foamtaine CAB/Velvetex BA35 | 7.50 |
| DeSulf TLS 40/Standapol T | 20.00 |
| Steol CA-460/Standapol EA 40 conc. | 10.00 |
| Foamid LC/Standamid KD | 2.00 |
| Ethylene Glycol Distearate | 1.00 |
| Vitamin E Acetate | 0.05 |
| Citric Acid | 0.50 |
| Sodium Chloride | 0.50 |
| Fragrance 3650 | 0.10 |
| Total | 100.00 |
| Conditioner | |
| Demineralized Water | 47.5483 |
| Melanin hydrolysate | 0.0015 |
| Triethanolamine | 0.04 |
| Gafquat 755N | 2.00 |
| Germaben II-E | 0.75 |
| Propylene Glycol | 5.00 |
| Biomin Cinque | 0.05 |
| Hydrocoll G-40 | 0.05 |
| Tween 20 | 0.50 |
| Fragrance 3650 | 0.01 |

| Ingredients | % |
| --- | --- |
| Aloe Extract HS | 0.05 |
| dl-Panthenol | 0.50 |
| Demineralized Water | 40.00 |
| Dow Corning 929 Emulsion | 3.50 |
| Total | 100.00 |
| Cream Rinse | |
| Demineralized Water | 73.0985 |
| Melanin hydrolysate | 0.0015 |
| Carsoquat SDQ 25 | 10.00 |
| Carsoquat CT-429 | 6.00 |
| Cetearyl Alcohol/Cetyl/Stearyl Alcohol | 8.00 |
| Hydrocoll G40 | 1.00 |
| Germaben II | 1.00 |
| dl-Panthenol | 0.50 |
| Aloe Extract HS | 0.10 |
| Vitamin E Acetate | 0.10 |
| Biomin Cinque | 0.10 |
| Fragrance 3650 | 0.10 |
| Total | 100.00 |

In the foregoing examples solubilized melanin was obtained by an enzymatic hydrolysis of melanin which formed the melanin hydrolysate, a liquid containing solubilized melanin and having a pH of about 6.8. The enzymatic hydrolysis included reacting 2% of an enzyme (Trypsin 1:80), 96% demineralized water, 0.2% melanin and 0.2% methyl paraben for several days at room temperature until complete solubility was reached. The material was then heated to about 90° C. for several minutes to destroy the enzyme and pH adjusted to 6.8 with concentrated hydrochloric acid. Amounts of sodium hydroxide to pH 10.5 and demineralized water are used to dilute the mixture such that 4 cc of the formed melanin hydrolysate liquid added to 500 g of a base yields a concentration of about 1.6 mg melanin per 100 g base.

The melanin may alternatively be solubilized by an effective amount of triethanolamine and oxidized by ferric chloride. The resulting mixture may then be mixed for 2-3 hours by ultrasound to break-up and further solubilize conglomerates. A solubilized melanin suspension results and may be combined with the pertinent base ingredients for topical application to the hair and scalp.

Equivalents

The above examples of the subject invention can be varied by those skilled in the art without departing from the fundamentals of the subject invention. Thus, it can be seen that the subject invention may be produced through the process of the present invention. The composition and method herein employ compositions of ingredients which may be safely used on the skin, scalp or hair. The invention may be used in the form of lotion, cream and ointment. The description herein is therefore considered in all respects as illustrative and limited in breadth and scope of the invention being indicated by the subsequent claims rather than by the foregoing description.

I claim:

1. A composition for protecting the skin against ultraviolet rays comprising:
   an effective amount of melanin;
   a substance for solubilizing melanin selected from the group consisting of triethanolamine and trypsin, the substance present in an amount sufficient to solubilize the melanin thereby producing melanin solubilized by the substance; and
   a vehicle for topical application in which the melanin solubilized by the substance is distributed.

2. A composition as claimed in claim 1 wherein the substance is triethanolamine present at a concentration of about 5 percent and greater.

3. A composition as claimed in claim 3 further comprising ferric chloride for oxidizing the melanin, the ferric chloride present in an amount sufficient to oxidize the melanin.

4. A composition as claimed in claim 1 wherein the vehicle is an ointment, cream or lotion.

5. A composition as claimed in claim 1 further comprising a preservative.

6. A composition as claimed in claim 1 further comprising aloe vera.

7. A composition as claimed in claim 1 further comprising sufficient amounts of a sunscreen, singly or in combination, to produce a composition having a sun protective factor of from about 1 to about 30.

8. A composition as claimed in claim 1 further comprising a free radical scavenger for absorbing free radicals generated in the skin upon exposure of the skin to ultraviolet rays.

9. A composition as claimed in claim 1 wherein the vehicle for topical application comprises ingredients selected from the group consisting of glyceryl cocoate, hydrogenated coconut oil, glyceryl, octyldimethyl PABA, propylene carbonate, cetearyl octanoate, d-Panthenol, mineral oil, trilaureth-4-phosphates, cetyl alcohol, sorbitol, carbopol, propylene glycol dicaprylate/dicaprate.

10. A method of making a composition for topical application to human skin to protect the skin against ultraviolet rays, the method comprising the steps of:
   solubilizing an effective amount of melanin with a substance selected from the group consisting of triethanolamine and trypsin that is present in an amount sufficient to solubilize the melanin, to thereby form solubilized melanin; and
   distributing the solubilized melanin in a base suitable for topical application to the skin.

11. A method of protecting human skin against ultraviolet rays, comprising the step of
   topically applying to the skin a composition comprising
   (a) an effective amount of melanin as an active ingredient
   (b) a substance selected from the group consisting of trypsin and triethanolamine for solubilizing the melanin, the substance present in an amount sufficient to solubilize the melanin, thereby providing solubilized melanin; and
   (c) a vehicle for topical application to the skin in which the solubilized melanin is distributed.

* * * * *

UNITED STATES PATENT AND TRADEMARK OFFICE
CERTIFICATE OF CORRECTION

PATENT NO. : 5,256,403
DATED      : October 26, 1993
INVENTOR(S): Frances C. Gaskin It is certified that error appears in the above-identified patent and that said Letters Patent is hereby corrected as shown below:

Column 8, line 14 before "further" delete "3" and insert instead --2--.

Signed and Sealed this

Twelfth Day of April, 1994

BRUCE LEHMAN

Attest:

Attesting Officer    Commissioner of Patents and Trademarks